(12) United States Patent
Downey et al.

(10) Patent No.: US 8,788,019 B2
(45) Date of Patent: Jul. 22, 2014

(54) SYSTEM AND METHOD FOR PERFORMING A BIOPSY OF A TARGET VOLUME AND A COMPUTING DEVICE FOR PLANNING THE SAME

(75) Inventors: Donal Downey, British Columbia (CA); Aaron Fenster, Ontario (CA)

(73) Assignee: Robarts Research Institute, London, Ontario (CA)

( * ) Notice: Subject to any disclaimer, the term of this patent is extended or adjusted under 35 U.S.C. 154(b) by 1771 days.

(21) Appl. No.: 11/885,177

(22) PCT Filed: Feb. 28, 2006

(86) PCT No.: PCT/CA2006/000282
§ 371 (c)(1),
(2), (4) Date: Dec. 15, 2008

(87) PCT Pub. No.: WO2006/089426
PCT Pub. Date: Aug. 31, 2006

(65) Prior Publication Data
US 2009/0093715 A1  Apr. 9, 2009

Related U.S. Application Data

(60) Provisional application No. 60/656,384, filed on Feb. 28, 2005.

(51) Int. Cl.
| | | |
|---|---|---|
| A61B 5/055 | (2006.01) | |
| A61B 8/08 | (2006.01) | |
| A61B 8/00 | (2006.01) | |
| A61B 8/12 | (2006.01) | |
| A61B 10/02 | (2006.01) | |
| A61B 19/00 | (2006.01) | |
| A61B 17/34 | (2006.01) | |
| A61B 17/00 | (2006.01) | |
| A61B 18/00 | (2006.01) | |

(52) U.S. Cl.
CPC ............ *A61B 8/4461* (2013.01); *A61B 8/0833* (2013.01); *A61B 10/02* (2013.01); *A61B 2019/5291* (2013.01); *A61B 19/50* (2013.01); *A61B 19/52* (2013.01); *A61B 2017/3411* (2013.01); *A61B 2019/505* (2013.01); *A61B 2019/5251* (2013.01); *A61B 2017/3413* (2013.01); *A61B 2019/5289* (2013.01); *A61B 2017/00274* (2013.01); *A61B 8/483* (2013.01); *A61B 2019/5276* (2013.01); *A61B 8/463* (2013.01); *A61B 2019/507* (2013.01); *A61B 2019/5265* (2013.01); *A61B 10/0241* (2013.01); *A61B 2018/00547* (2013.01); *A61B 2019/5255* (2013.01); *A61B 8/4209* (2013.01); *A61B 19/5244* (2013.01); *A61B 17/3403* (2013.01); *A61B 8/12* (2013.01); *A61B 2019/5295* (2013.01)
USPC ............................ 600/424; 600/437; 600/567

(58) Field of Classification Search
USPC ......................................... 600/424, 437, 567
See application file for complete search history.

(56) References Cited

U.S. PATENT DOCUMENTS

| | | | | |
|---|---|---|---|---|
| 5,868,673 | A * | 2/1999 | Vesely | 600/407 |
| 5,956,418 | A * | 9/1999 | Aiger et al. | 382/154 |
| 6,064,904 | A * | 5/2000 | Yanof et al. | 600/414 |
| 6,206,832 | B1 | 3/2001 | Downey et al. | |
| 6,238,342 | B1 | 5/2001 | Feleppa et al. | |
| 6,379,302 | B1 * | 4/2002 | Kessman et al. | 600/437 |
| 6,390,982 | B1 | 5/2002 | Bova et al. | |
| 6,512,943 | B1 * | 1/2003 | Kelcz | 600/436 |
| 6,524,247 | B2 | 2/2003 | Zhao et al. | |
| 6,546,279 | B1 * | 4/2003 | Bova et al. | 600/429 |
| 6,669,635 | B2 * | 12/2003 | Kessman et al. | 600/437 |
| 6,824,516 | B2 * | 11/2004 | Batten et al. | 600/439 |
| 6,968,224 | B2 * | 11/2005 | Kessman et al. | 600/407 |
| 7,496,398 | B2 * | 2/2009 | Nields et al. | 600/427 |
| 2003/0135115 | A1 * | 7/2003 | Burdette et al. | 600/437 |
| 2004/0171924 | A1 | 9/2004 | Mire et al. | |
| 2005/0085717 | A1 * | 4/2005 | Shahidi | 600/424 |
| 2005/0085718 | A1 * | 4/2005 | Shahidi | 600/424 |
| 2005/0159676 | A1 | 7/2005 | Taylor et al. | |
| 2005/0182316 | A1 * | 8/2005 | Burdette et al. | 600/424 |
| 2006/0004275 | A1 * | 1/2006 | Vija et al. | 600/407 |
| 2006/0149147 | A1 * | 7/2006 | Yanof | 600/424 |

| | | | |
|---|---|---|---|
| 2007/0276234 | A1* | 11/2007 | Shahidi .......................... 600/437 |
| 2008/0004526 | A1* | 1/2008 | Gross ............................ 600/437 |
| 2008/0039713 | A1* | 2/2008 | Thomson et al. ............. 600/411 |
| 2008/0091101 | A1* | 4/2008 | Velusamy et al. ............ 600/427 |
| 2008/0146916 | A1* | 6/2008 | Okerlund et al. ............. 600/424 |
| 2008/0186378 | A1* | 8/2008 | Shen et al. ..................... 348/65 |

FOREIGN PATENT DOCUMENTS

| | | |
|---|---|---|
| WO | WO 96/25881 | 8/1996 |
| WO | WO 01/89384 | 11/2001 |
| WO | WO 03/032837 | 4/2003 |
| WO | WO 2004/019799 | 3/2004 |

OTHER PUBLICATIONS

European Search Report dated Dec. 15, 2009 in corresponding European Application No. 06705236.5.
Canadian Office Action dated May 31, 2012 in corresponding Canadian Appl. No. 2,600,981.
European Examination Report dated May 3, 2012 in corresponding European Appl. No. 06705236.5.

* cited by examiner

Primary Examiner — Long V. Le
Assistant Examiner — Angela M Hoffa
(74) Attorney, Agent, or Firm — Russell T. Manning; Marsh Fischmann & Breyfogle LLP

(57) ABSTRACT

A system and method for performing a biopsy of a target volume and a computing device for planning the same are provided. A three-dimensional ultrasound transducer captures ultrasound volume data from the target volume. A three-dimensional registration module registers the ultrasound volume data with supplementary volume data related to the target volume. A biopsy planning module processes the ultrasound volume data and the supplementary volume data in combination in order to develop a biopsy plan for the target volume. A biopsy needle biopsies the target volume in accordance with the biopsy plan.

14 Claims, 8 Drawing Sheets

SYSTEM AND METHOD FOR PERFORMING A BIOPSY OF A TARGET VOLUME AND A COMPUTING DEVICE FOR PLANNING THE SAME

CROSS-REFERENCE TO RELATED APPLICATIONS

This application claims the benefit of U.S. Patent Application Ser. No. 60/656,384 filed on Feb. 28, 2005.

FIELD OF THE INVENTION

The present invention relates generally to imaging systems and, specifically, to a system and method for performing a biopsy on a target volume and a computing device for planning the same.

BACKGROUND OF THE INVENTION

Prostate Cancer (PCa) is the most commonly diagnosed malignancy in men, and is found at autopsy in 30% of men at the age of 50, 40% of men at age 60, and almost 90% of men at age 90. Worldwide, it is the second leading cause of death due to cancer in men, accounting for between 2.1% and 15.2% of all cancer deaths. In Canada, 18,800 new PCa cases were diagnosed (26% of all new cancers in men) and 4,200 men died from this disease in 2003. In the United States, 189,000 new cases were diagnosed and 30,200 died from PCa in 2002. When diagnosed at an early stage, the disease is curable, and even at later stages treatment can be effective. Once the tumor has extended beyond the prostate, however, the risk of metastases increases. In managing patients with possible PCa, the challenges facing physicians are to: (a) diagnose clinically relevant cancers at a curable stage, (b) stage the disease accurately, (c) apply the appropriate therapy accurately to destroy cancer cells while preserving normal tissues, and (d) follow patients to assess side effects and therapy effectiveness.

Definitive diagnosis of PCa involves the detection of cancerous tissue obtained from the prostate during biopsy. Ultrasound-guided biopsy methodologies such as for the detection of prostate cancer are well-known and require needles to be inserted into the body to obtain a biopsy sample of one or more target tissue areas. Historically, these biopsy methodologies have been inaccurate. The introduction of trans-rectal ultrasound ("TRUS") has revolutionized prostate biopsy techniques and has greatly increased the accuracy of biopsy. Widespread screening for PCa using the prostate-specific antigen ("PSA") test has greatly increased the numbers of TRUS-guided biopsy. While TRUS-guided prostate biopsy has become a commonly-performed urological procedure, it is not without limitations and controversy. Chief among the problems facing urologists daily relates to the management of patients in whom a first set of prostate biopsies were negative for cancer. Since the prostate volume sampled by the biopsy is small and PCa is often multifocal, involving only a small volume of the prostate in the early stages of the disease, may result in a false negative biopsy. The end result is patients harboring cancer at early and curable stages. Management of these patients, as well as those diagnosed with early stage disease, has generated a great deal of debate and controversy, driving the need for improved prostate biopsy techniques to help resolve.

The controversies related to the decision of how best to manage early-stage PCa are among the most intensely debated in all of clinical medicine by medical professionals as well as concerned patients. Management options for early-stage PCa are: "watchful-waiting", hormone therapy, surgery and radiotherapy. Since the natural history of PCa is long and many patients diagnosed with PCa are elderly, some have argued that "watchful-waiting" is appropriate. Patients with intermediate-grade and high-grade cancers, however, can have a substantial risk of early local failure if an intervention is not undertaken. Clearly, in order to provide the patient with the best and most appropriate treatment option, an accurate prostate biopsy procedure is crucial in obtaining sufficient cancerous tissue for grading if cancer is present.

Various reports have shown that the detection rate on repeat biopsy ranges between 10% to 25% (after the first biopsy was negative). Although advances in technology and understanding of the disease have produced improvements in the biopsy procedure, significant dilemmas and technical challenges clearly remain. For example, if an initial biopsy fails to detect cancer, who should undergo a repeat biopsy? How should a repeat biopsy be directed? Should the repeat (and initial) biopsy be lesion-directed, random, or based on the details of the patient's anatomy (e.g., prostate regions, volume, shape).

Worldwide, the most common indication for prostate biopsy is the presence of serum PSA levels greater than 4.1 ng/ml. Because a significant proportion of men with PSA in the 2.5 to 4.0 ng/ml range have PCa, some investigators have advocated decreasing the PSA threshold to enhance PCa detection. While early detection may increase the probability that the disease is confined to the prostate and that such patients are more likely to be free of PSA failure with improved disease-free survival after treatment, lowering the threshold significantly increases the numbers of patients treated for non-lethal PCa. Despite the ongoing debate and lack of a general consensus at this time, some centers have lowered the threshold for younger men, significantly increasing the numbers of prostate biopsies performed. As lowering this threshold results in biopsies of prostates with a small volume of cancer, improved biopsy techniques are clearly required to increase the yield on the first biopsy and improve the planning of the potentially increasing numbers of repeated biopsies.

In many cases, significant discomfort is reported during the biopsy procedure. After biopsy, common side-effects include hematuria, hematospermia and hematochezia in about a third to a half of patients. Although these are relatively minor, there is a potential for other less frequent post-biopsy morbidity including sepsis (0.2%-0.6%), urinary tract infection (0.1%-4.5%) and urinary retention (0.2%-1.2%). As a result, it is desirable to reduce the frequency of such procedures.

The optimal distribution of cores within the prostate has been studied extensively, and it has been shown that uniform biopsy approaches such as sextant methods are subject to sampling limitations in view of the wide variations in gland sizes. This issue has been explored using computer simulations of the biopsy procedure and prostate anatomy, with probability distribution of location, frequency and volume of prostate carcinoma obtained from radical prostatectomy specimens. Results from computer simulations and clinical studies, which explored different systematically distributed cores, have demonstrated that the positive biopsy yield depends on the magnitude of gland sampling. Increasing the number of biopsy cores increases the biopsy yield, and this effect is most pronounced in larger prostates. Using the same number of cores regardless of individual prostate characteristics may lead to over-sampling of small glands, and less extensive and potentially inadequate sampling of large glands.

With more men undergoing PSA testing and the potentially lowered PSA threshold for prostate biopsy, physicians commonly face the dilemma of the patient with a negative prostate biopsy who still has suspicious clinical exam or serum PSA results. With the limited informational value of a negative biopsy, and that no evidence of cancer on biopsy does not preclude the possibility of a missed cancer, patients are often required to undergo repeat biopsies when clinical suspicion exists and in cases when a positive biopsy for cancer would have therapeutic consequences. Since there are an appreciable number of men with false-negative biopsy who in fact harbor curable PCa, the medical science is faced with a difficult challenge.

Many investigators have examined the positive yields on repeated biopsies of men with elevated PSA or suspicious digital rectal exam ("DRE") or TRUS finding. The results demonstrated that on the first biopsy, about 15% to 40% of men had PCa, about 15% to 23% of men had PCa on the second biopsy and 8% to 10% of men had PCa on the third biopsy. In some of the patients with false-negative biopsy, the cancer might be clinically insignificant, warranting no therapy, but some of these patients might benefit from detection and subsequent treatment.

Another important challenge facing physicians is in men diagnosed on biopsy to have pre-malignant lesions, i.e. high-grade prostatic intraepithelial neoplasia ("PIN"), and particularly atypical small acinar proliferation ("ASAP"). These are challenging to manage as there is a 40% to 50% chance of finding cancer on repeat biopsy with ASAP. Since co-existing cancer might be present, especially with ASAP, where the pathologist finds only a small amount of histologic "atypia" but not enough material to confidently diagnose cancer, these patients typically undergo a repeat biopsy soon after the first. In these situations, it is important to re-biopsy the same area to increase the yield. Currently, only a vague location of the abnormal findings is available, and it is not possible to be certain that the same area has been sampled on the repeat biopsy.

As a result of the increasing number of younger men with potentially early and curable PCa undergoing repeated prostate biopsy, it is therefore important not to re-biopsy the same area if the original biopsy was negative, and it is particularly important to re-biopsy the exact area if a possible abnormal area was detected on first biopsy as ASAP. Thus, improved guidance to suspicious regions of the prostate using information from other modalities is desired, as well as the locations of the cores obtained from the prostate must be known accurately to help guide the physician during the repeat biopsy, in order to help in correlating any imaging evidence of the disease and provide improved planning for the subsequent therapy.

It is, therefore, an object of the present invention to provide a novel system and method for performing a biopsy on a target volume and a computing device for planning the same.

SUMMARY OF THE INVENTION

In an aspect of the invention, there is provided a system for performing a biopsy of a target volume, comprising:

a three-dimensional ultrasound transducer for capturing ultrasound volume data from said target volume;

a three-dimensional registration module for registering said ultrasound volume data with supplementary volume data related to said target volume;

a biopsy planning module for processing said ultrasound volume data and said supplementary volume data in combination in order to develop a biopsy plan for said target volume; and a biopsy needle for biopsying said target volume in accordance with said biopsy plan.

In another aspect of the invention, there is provided a method for performing a biopsy of a target volume, comprising:

obtaining ultrasound volume data of said target volume using a three-dimensional ultrasound transducer;

registering said ultrasound volume data with supplementary volume data related to said target volume; and processing said ultrasound volume data and said supplementary volume data in combination in order to develop a biopsy plan for said target volume.

In accordance with a further aspect of the invention, there is provided a computing device for planning a biopsy of a target volume, comprising:

a three-dimensional registration module for registering ultrasound volume data with supplementary volume data related to said target volume;

a biopsy planning module for processing said ultrasound volume data and said supplementary volume data in combination in order to develop a biopsy plan for said target volume.

By combining 2D/3D TRUS imaging with supplementary volume data such as functional imaging from another imaging modality, information from multiple sources, modalities and/or times can be cross-correlated to enhance the guidance of prostate biopsy or, in fact, biopsy of other organs such as the breast.

BRIEF DESCRIPTION OF THE DRAWINGS

Embodiments will now be described, by way of example only, with reference to the attached Figures, wherein.

DETAILED DESCRIPTION OF THE EMBODIMENTS

PCa diagnosis is established by histological examination of prostate tissue obtained most commonly by TRUS-guided biopsy and sometimes by trans-urethral resection procedures ("TURP"). Needle biopsy of the prostate represents the only definitive diagnostic modality capable of confirming malignancy in men with palpable and ultrasonically undetected lesions, and is now always performed under ultrasound guidance. Indications for initial prostate needle biopsy are well established, consisting of any abnormality on DRE or an abnormal PSA result, although the PSA threshold for biopsy is being re-examined. Typically, prostate lesions detected with DRE and TRUS have two or three cores taken through them. Since many small prostate cancers are not detected with TRUS or DRE, needle samples are obtained from predetermined regions of the prostate that are known to have high probability of harboring cancer. These are typically in the peripheral zone (PZ) (which harbors 80% of all prostate cancers and a higher proportion of clinically significant ones), and close to the capsule, as most cancers are thought to start within 5 mm of the prostate capsule. Traditionally, the predetermined biopsy pattern has included 6 core biopsies, but as this has been shown to miss approximately 20% of cancers. As a result, most centers are now taking 8 or more PZ tissue core samples as part of their routine assessment.

Biopsies are typically performed with a thin, 18-guage needle mounted on a spring-loaded gun connected to the ultrasound ("US") probe, forcing the needle to stay in the imaging plane so that it is always visible in the US image. The location of each core is registered, so that the pathologist can report the extent and grade of the cancer. This is especially important if the histological result is equivocal and the pathologist requests a repeat biopsy. It is, therefore, important to know from what exact location the=sample was obtained in order to target more relevant tissue if a repeat biopsy is performed.

Figure 1:
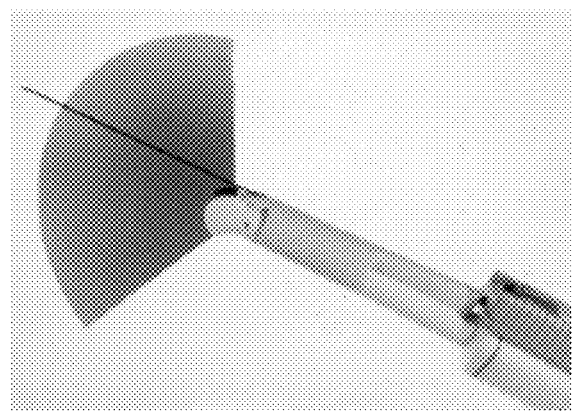
FIG. 1 is a schematic diagram of a three-dimensional (3D) trans-rectal ultrasound ("TRUS") transducer and needle guide.

FIG. 1 shows a TRUS with an attached biopsy guide that holds a needle. The needle extends into the plane of the TRUS image so that it is continuously visible therein.

Figure 2:
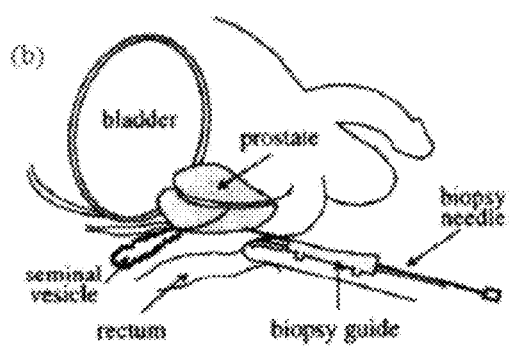
FIG. 2 shows the 3D TRUS transducer positioned inside a patient.

FIG. 2 illustrates the TRUS of FIG. 1 during the performance of a prostate biopsy.

Figure 3:
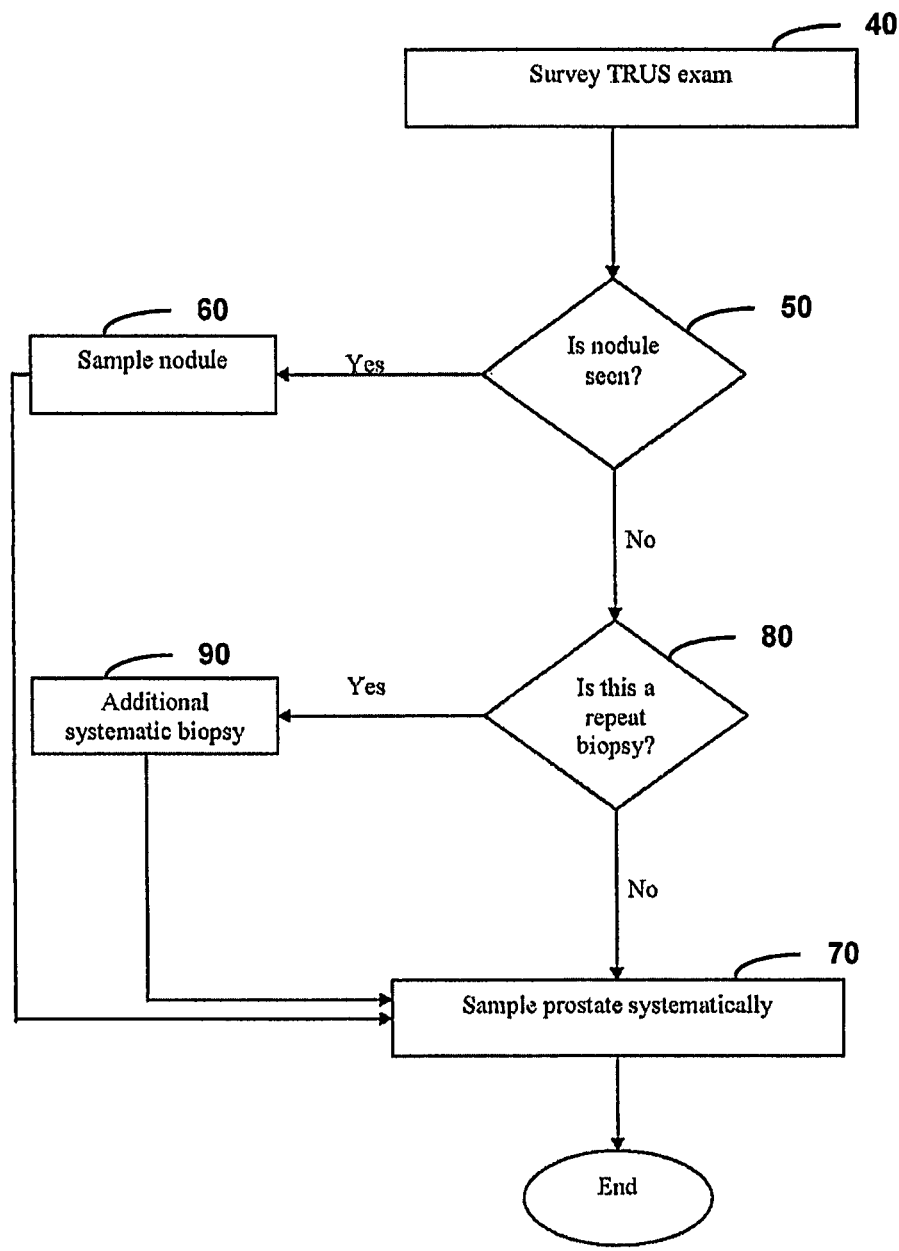
FIG. 3 is a flowchart of the conventional method of performing a prostate biopsy.

FIG. 3 shows the steps performed during a conventional biopsy. The two most common reasons that people are referred for prostate biopsy are the detection of an abnormality in their serum PSA or during an evaluation of their prostate with a DRE.

During administration of DRE, the patient is subjected to pre-treatment involving a course of prophylactic antibiotics, and the administration of a rectal/lower large bowel cleaning protocol. The patient is then positioned on a bed, lying on their left side with their hips and knees fully flexed. The examiner introduces a copious amount of gel into the rectum with their finger and subsequently introduces an "end-fire" TRUS into the rectum of the patient. The US image parameters are immediately adjusted to ensure optimal image quality and the prostate is evaluated in two planes using B Mode (always) and Color or Power Doppler (in some cases).

The prostate is measured during a survey TRUS examination (step 40). A variety of measurement protocols are used; the most common presumes the prostate is an ellipse and its volume is calculated by multiplying its longest length by its longest width by its longest AP diameter by 0.52.

After completing the survey TRUS examination, the operator decides if there is any "nodule" in the prostate that is suspicious for a focal cancer (step 50). The operator may feel a focal anomaly prior to imaging, detect a non-compressible hypoechoic mass, detect architectural distortion, focal hypervascularity or marked asymmetry. Alternatively, a prior biopsy may have identified an "area suspicious for malignancy" and the pathologist may have recommended re-biopsy of this. This area would also be treated like a "nodule" for biopsy protocol reasons.

If a "nodule" is detected at step 50, then a nodule biopsy protocol is followed (step 60). Otherwise a "no nodule" protocol is adhered to.

During the nodule biopsy protocol, the operator plans to obtain a pre-determined number of samples from the nodule—typically either two or three 18-gauge core samples. Once the sampling of the nodule is planned, the sampling of the rest of the prostate is also planned in a systematic way (step 70). This typically would consist of obtaining about another eight samples from pre-determined locations in the peripheral zone and possibly a small number from the central gland.

During the no nodule biopsy protocol, the operator plans to obtain a pre-determined number of samples from the peripheral zone of the prostate. The original pattern (the sextant pattern) called for six peripheral zone samples; one from the base, one from the middle and one from the prostate apex on either side. Newer protocols typically have an increased number of samples being obtained from the peripheral zone with increased emphasis of sampling from the lateral part of the gland. Most protocols nowadays involve ten or twelve samples.

If it is determined at step 80 that this is a repeat biopsy, additional systematic biopsies are planned (step 90). The "No Nodule Biopsy Protocol" is typically altered if the patient has had a prior negative biopsy and yet clinically and biochemically remains suspicious for disease. These protocols typically call for increasing the number of peripheral zone biopsy, possibly altering the location of some of these biopsies and also taking some samples from the transition zone.

If any additional sample biopsies have been planned, the prostate is sampled systematically at step 70.

With the planned biopsy template mentally "worked out" in the operator's mind, local anesthesia may be administered. This usually consists of Xylocaine 1% or 0.5% administered either about the neurovascular bundles, into the periprostatic space or directly into the prostate. The operator then surveys the prostate in either the sagittal or transverse plane using a transducer such as that shown in FIG. 1 and applies the mental template to the prostate and acquires the samples. This is an inexact process but typically the "mid peripheral zone" is assigned to that portion of the gland that is at the level of the veru montanum. The apex is typically the region of the prostate within 1.5 cm of the external sphincter and the base that portion of the gland within 1.5 cm of the superior border of the gland. No record of where the samples were obtained is typically recorded.

Most operators obtain samples from the base of the gland initially, the mid and apical regions subsequently and finally from the transition zones, if they need to be sampled. Any periprostatic bleeding, rectal wall bleeding or rectal luminal bleeding is typically treated with direct compression for periods of three to ten minutes. Following a brief period of bed rest the patient is allowed to resume light activity in the hospital or office for periods between twenty to sixty minutes. If the patient is well following this, he is discharged.

While it may be theoretically obvious to the operator where the protocol requires biopsies to be obtained, applying the mental template to the actual prostate is challenging as "end-firing" images are not orthogonal to the long axis or transverse axis of the prostate. After samples have been obtained, it is often not clear exactly where they were taken from and that locations are often not recorded. This poses an especially challenging problem in cases where the pathologist may have recommended re-biopsy of a specific region.

The conventional approach for performing biopsies can result in a lower than desired level of care for many patients as much clinical, biochemical and imaging information is not being considered during the sampling process.

Figure 4:
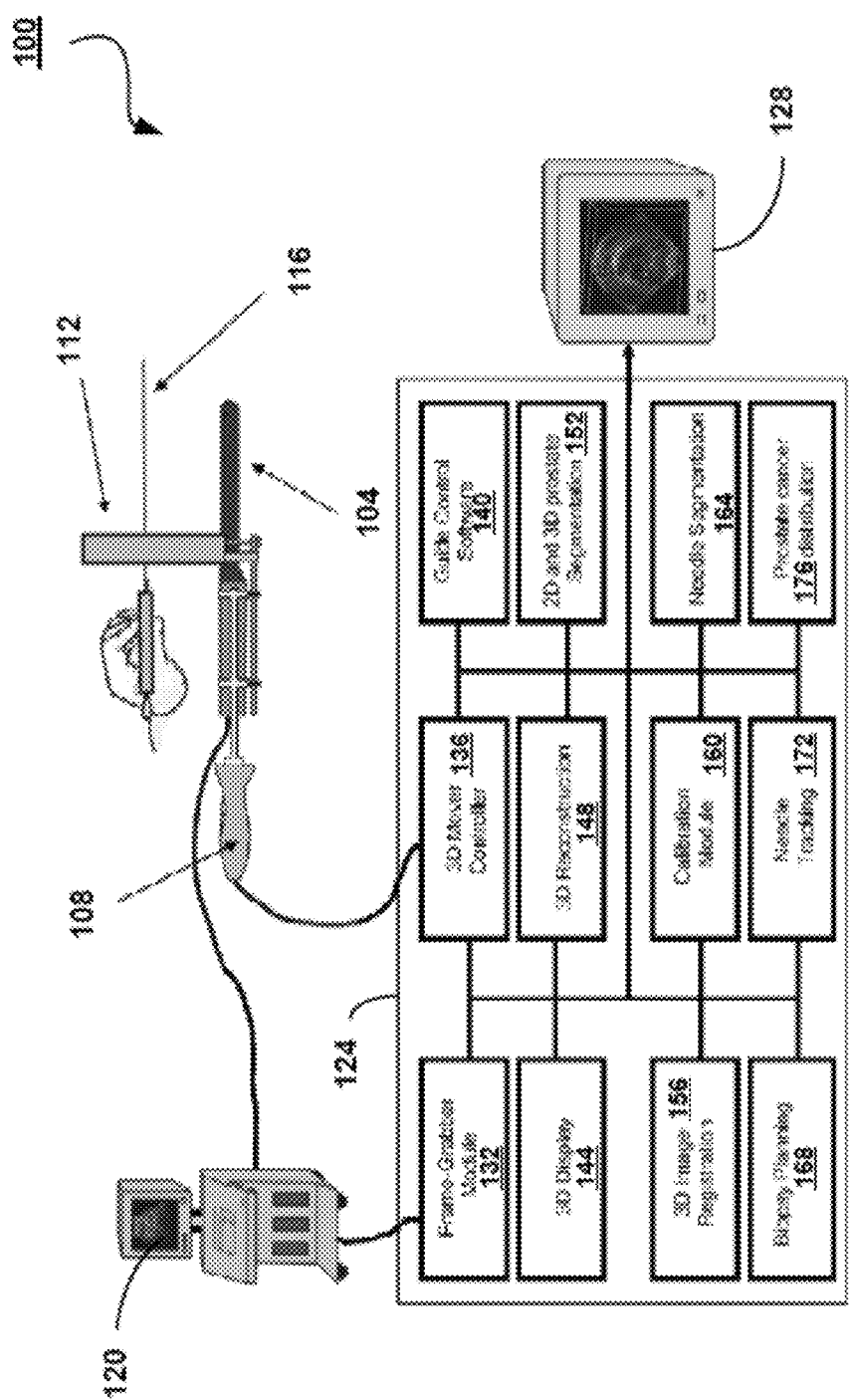
FIG. 4 is a schematic diagram of one embodiment of a system for performing a biopsy.

A system for performing biopsies that helps to alleviate the above disadvantages is shown generally at 100 in FIG. 4. The system 100 includes a TRUS transducer 104 coupled to a motor assembly 108 that operates to control the longitudinal movement and rotation of the TRUS transducer 104. The TRUS transducer 104 is operable to continuously capture radial 2D US images over a radial operational scan range. A needle guide 112 is coupled to the TRUS transducer 104. The needle guide 112 is a multiple-holed template used to stabilize lateral movement of a needle 116. The needle 116 is used to extract biopsy cores from the prostate of a patient. The TRUS transducer 104 is also coupled to a conventional US machine 120 for displaying image data as it is captured by the TRUS transducer 104. The motor assembly 108 and US machine 120 are in communication with a computer 124. A display 128 is coupled to the computer 124 for presenting images generated by the computer 124.

The computer 124 is a personal computer having a processor that executes software for performing 3D image acquisition, reconstruction and display. The processor also executes software for performing biopsy planning, and for controlling the TRUS transducer 104. The computer 124 includes a video frame-grabber 132, a 3D mover controller module ("MCM") 136, a guide control module 140, a 3D display module 144, a 3D reconstruction module 148, a 2D and 3D prostate segmentation module 152, a 3D image registration module 156, a calibration module 160, a needle segmentation module 164, a biopsy planning module 168, a needle tracking module 172 and a prostate cancer distribution module 176.

The video-frame grabber 132 captures image data from the US machine 120 and preferably operates at 30 Hz or greater to provide rapidly updated ultrasound images. Such a module for acquiring and storing 2D US images is described in U.S. Pat. Nos. 5,457,371 and 5,562,095. The MCM 136 is coupled to and controls the motor assembly 108. In turn, the motor assembly 108 controls the longitudinal and rotational movement and the image data acquisition timing of the TRUS transducer 104. The guide control module 140 controls movement of the needle guide 112 perpendicular to the axis of the TRUS transducer 104 in order to accurately align holes of the needle guide 112 with a desired needle path. The user interface for the 3D display module 144 is described in U.S. Pat. Nos. 5,842,473 and 6,334,847.

The 3D display module 144 renders 3D images to be presented on the display 128 using the image data captured and processed by the imaging software. In particular, the 3D display module 144 generates three orthogonal views of the target volume: two that are co-planar to the needle 116 and a third that generally bisects the trajectory of the needle 116.

The 3D reconstruction module 148 receives 2D US images from the video frame-grabber 132 and, using a priori knowledge of the characteristics of the TRUS transducer 104, generates 3D images of the volume scanned. The 2D and 3D prostate segmentation module 152 analyzes the 2D images captured by the video frame-grabber 132 and the 3D images generated by the 3D reconstruction module 148 and distinguishes between the prostate and other tissue. The 3D image registration module 156 registers the 3D images received from the video frame-grabber 132 or from other sources with one another. The calibration module 160 calibrates the position of the needle guide 112 with the position of the TRUS transducer 104. The needle segmentation module 164 identifies needles in 2D and 3D US images.

The biopsy planning module 168 selects a biopsy plan based on a number of factors. These factors include the shape of the prostate determined by the 2D and 3D segmentation module 152, the location of any nodules in the 3D US images generated by the 3D construction module 148, the 3D images of other modalities received from other sources and general PCa probability distribution information. In response, the biopsy planning module 168 generates and provides planned needle trajectory information to the 3D visualization software so that the planned needle trajectory can be overlaid atop the US images on the display. The actual needle trajectory can then be viewed in relation to the planned needle trajectory. The biopsy planning module 168 can also receive and process the US images from the 3D reconstruction module 148 and dynamically re-determine the biopsy plan based on the actual needle trajectory and previous biopsy locations.

The needle tracking module 172 registers the location of the needle 116 and, thus, the location from which biopsies are being taken. The prostate cancer distribution module 176 determines a probability distribution for PCa based on parameters provided about the patient.

Figure 5:
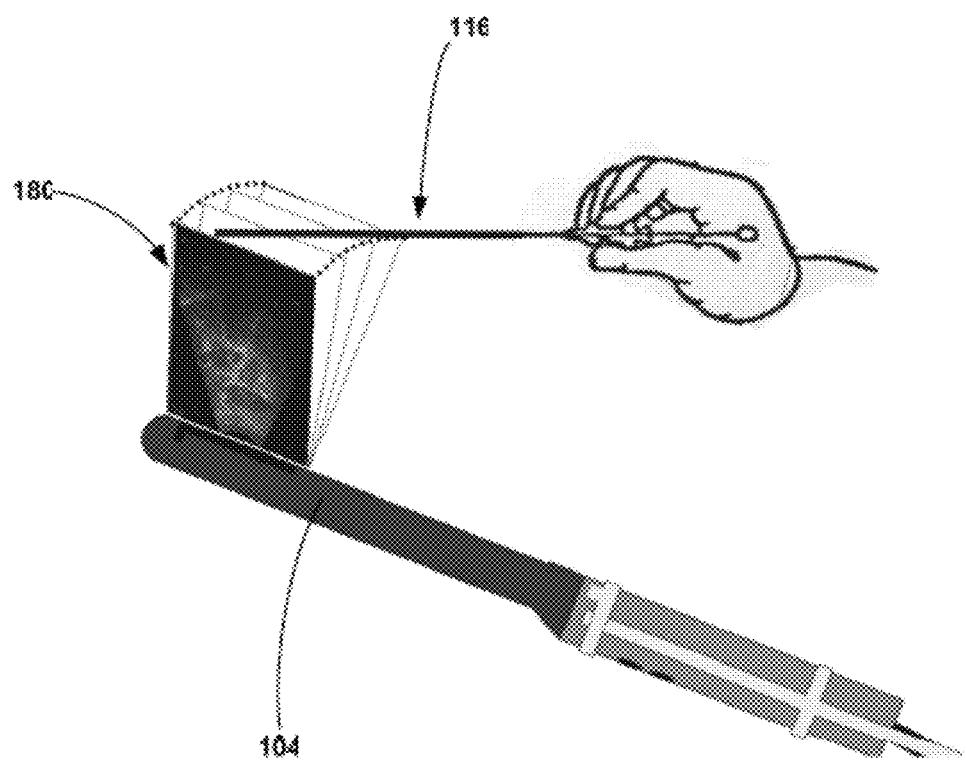
FIG. 5 shows the imaging of a biopsy needle by the 3D TRUS transducer of FIG. 1.

FIG. 5 shows the TRUS transducer 104 capturing a set of 2D US images. As the TRUS transducer 104 is rotated by the MCM 136, it captures image data to generate a series of 2D images 180. The 2D images 180 are captured at generally regular intervals during rotation of the TRUS transducer 104. Initially, the TRUS transducer 104 captures a 2D image 180 every one degree of rotation and rotates through 100 degrees, thereby capturing one hundred and one 2D images 180. The captured 2D images 180 are fanned radially in relation to the TRUS transducer 104. As will be understood, insertion of the needle 116 along an oblique trajectory results in the intersection of the 2D TRUS image planes. As a result, the needle 116 only appears as a point in the captured 2D US images.

Figure 6:
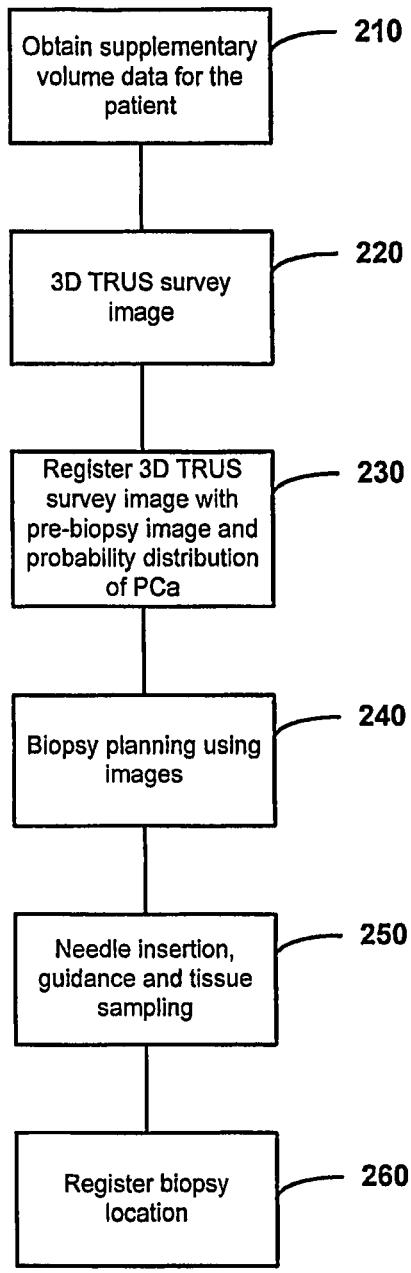
FIG. 6 is a flowchart that illustrates the method of performing a biopsy using the system of FIG. 4.

A method 200 for performing a biopsy that makes use of the system 100 will now be described with reference to FIG. 6. The method 200 enables the presentation of 3D images from multiple modalities, prostate cancer probability distributions, previous biopsies, etc.

The method 200 commences by obtaining supplementary volume data for the patient (step 210). A 3D TRUS survey image is captured (step 220). The 3D TRUS survey image is registered with the pre-biopsy image and a probability distribution of PCa (step 230). Biopsy planning is then performed using the images (step 240). Next, biopsy needle insertion is performed, with guidance from the system 20 and tissue is sampled (step 250). Using the detected location of the needle 116, the biopsy location is registered for future use (step 260).

During the obtaining of the supplementary volume data for the patient at step 210, at least one pre-biopsy functional 3D image of the patient's prostate generated using at least one other modality is received. These images can be received from another computing device via a communications interface (not shown) of the computer 124. The functional image may be based on a photon emitting radiopharmaceutical as in single photon emission computerized tomography ("SPECT") or with a gamma camera, or a positron emitting radiopharmaceutical as in positron emission tomography ("PET"). The radiopharmaceutical based images show abnormal uptake of the injected drug in regions of the prostate that may harbor malignant cells. In all cases, the functional image is obtained together with an anatomical image for use in registration as described later. The combined functional image and anatomical image is now routinely obtained with conventional imaging systems such as PET/computed tomography ("CT") scanners.

In addition, the supplementary volume data also includes a PCa probability distribution generated using information about the patient. This PCa probability distribution is provided as a color overlay on the 3D prostate image. The probability distribution of PCa is modified using the following non-imaging parameters:

Demographics—Race: The incidence and prevalence of prostate cancer is highest in African Americans. They typically have a higher occurrence of cancer, an acute Gleason grade in particular, and it typically occurs at a younger age than evidenced in other races. In contrast, orientals have the lowest incidence and prevalence of PCa.

Demographics—Age: Prostate cancer increases in incidence and prevalence with age.

Demographics—Family History: Having a first-degree relative (brother, father) with PCa almost doubles one's risk of getting the disease. Having a first-degree relative with breast cancer also increases the risk. A small minority of patients with specific genetic mutations is at a particularly high risk of prostate cancer.

Demographics—Geography: There is some evidence that living in particular geographic location may increase the risk of prostate cancer though this research is incomplete. Preliminary data suggests for example that there is a higher incidence and prevalence of PCa in the northern United States and Canada compared with the southern United States.

Demographics—Diet and Body Mass Index: A positive correlation between the risk of cancer and the body mass Index has been postulated and there is some evidence to support it. Specific foods are also being investigated to see if they have a protective effect against PCa. These include vitamin E, Selenium and soy products.

Biochemical Tests—PSA: PSA arguably has had the biggest influence on the survival rate of PCa patients in the last decade. It has enabled cancer to be detected at an earlier stage and has also been used to evaluate the impact specific treatments have had on individual patients. While the "absolute" level of serum PSA has some utility, integrating this number with other information is proving much more useful clinically. Below are some of these "integrated" PSA parameters that have proved useful.

Age-Specific PSA: Initially, a serum PSA of 4 ng/ml or less was considered normal. In recent years, most centers have adopted an age specific PSA which takes into account that the "normal" serum PSA increases with age. So, for example, a 45 year old with a PSA of greater than 2.5 ng/ml would be considered abnormal and a 75 year old with a PSA of less than 5.5 ng/ml would be considered normal.

PSA Density: That is, serum PSA/Prostate volume. Most people with a serum PSA greater than 4 ng/ml do not have prostate cancer. One of the commonest non-cancerous reasons for an elevated PSA is due to the presence of benign prostatic hyperplasia (BPH). By correcting the serum PSA for prostate volume many unnecessary biopsies could be avoided without clinically significant cancers being missed. Some authors have contended that correlating the serum PSA with the volume of the TZ on the prostate would be even more helpful clinically.

PSA Velocity: This is the rate of increase in serum PSA year over year. In recent years, increased emphasis has been put on detecting cancers at an earlier and earlier time, often before the PSA is greater than 4 ng/ml. PSA velocity is one of the tools that has shown some utility in this cohort, with several authorities recommending that patients be biopsied if the year over year increase in serum PSA is greater than 25%.

"Free to Total PSA ratio": PSA exists in different forms in the blood. Researchers have found that in patients with PCa most of the PSA is bound with carrier molecules and very little of it is "free" or unbound. In contrast, patients with BPH changes have a higher proportion of their PSA in "free" or unbound format. Several groups have found this useful in decreasing the number of unnecessary biopsies.

Biochemical Tests—Other: Serum Alkaline phostatase in often elevated in cases of metastatic prostate cancer. There are several other biochemical markers currently under evaluation.

Physical Exam—DRE: Signs of prostate cancer on DRE include a palpable mass, gross asymmetry and a "fixed" prostate.

Physical Exam—Other: Typically there are no other signs of prostate cancer until late in the disease. Then evidence of local spread and metastases such as bone pain, pathological fractures, hematuria and bladder dysfunction may be evident.

Pathology Findings—High-Grade PIN or ASAP: High-grade prostate intra-epithelial neoplasia (PIN) or atypical small acinar proliferation (ASAP) are precancerous conditions that almost always lead to a follow up series of biopsies. While controversy currently exists about how and when to re-biopsy these patients, protocols are under construction. The risk is real with some studies reporting as high as 50% chance of malignancy in patients with ASAP at the time of the first re-biopsy.

Still further, the supplementary volume data includes 2D and 3D images of the locations of any previous biopsies performed on the patient. These images are registered and stored during previous biopsy procedures and are retrieved in order to assist biopsy planning.

During the performance of the 3D US survey image at step 220, the TRUS transducer 104 is inserted into the patient as shown in FIG. 2. The MCM 136 directs the motor assembly 108 to cause the TRUS transducer 104 to rotate about its long axis over about 100 degrees while image data corresponding to 2D US images is captured at one degree intervals. The image data corresponding to the 2D US images is then transmitted to the computer 40 to be digitized by the video frame-grabber 132 and registered.

The acquired 2D US images are processed by the 3D reconstruction module as they are collected. The 2D US images correspond to planes radially extending from the central axis of rotation of the TRUS transducer 104. Accordingly, the 3D volume is reconstructed by translating and rotating the 2D US images with respect to one another. The reconstructed 3D volume consists of an array of voxels, or 3D pixels. The voxels are typically cubic (but can also be rhomboidal) and are arranged according to a 3D Cartesian system. Each voxel is assigned a greyscale-level value based on the greyscale-level values of the pixels in the translated 2D images adjacent to it.

Figure 7:
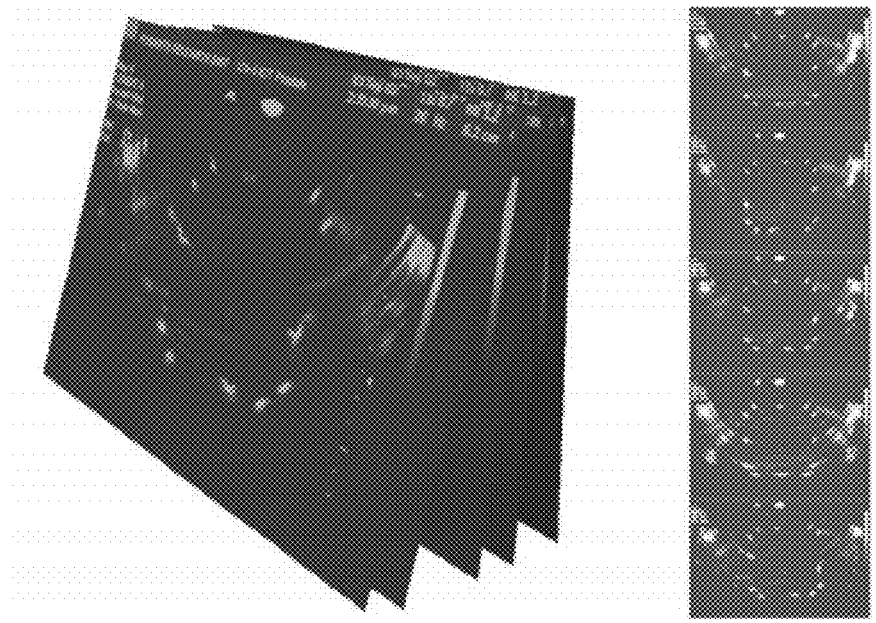
FIG. 7 is a diagram showing five two-dimensional ("2D") ultrasound ("US") images and their relative orientation.

FIG. 7 illustrates a set of five 2D US images that have been translated to their relative positions. As shown, the 2D US images are radially fanned.

Figure 8:
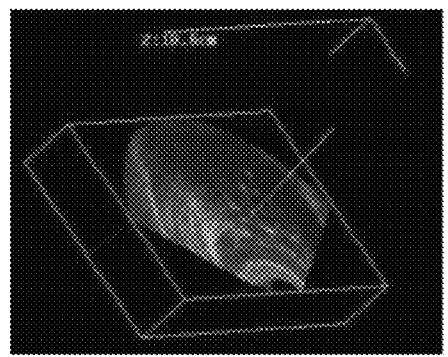
FIG. 8 shows a volume reconstructed from a series of 2D US images captured using the 3D TRUS transducer of FIG. 1.

FIG. 8 illustrates a 3D US image reconstructed from the set of 2D US images. As can be seen, the 3D US image has a fan profile corresponding to the volume imaged by the TRUS transducer 104. The acquired 2D US images are reconstructed into a 3D US image by the 3D reconstruction module 148. The 3D US display module 144 then generates a view of the 3D US image, and provides a multi-planar 3D display and volume rendering, as well as an extensive set of measurement tools. The 3D US image is then presented for viewing on the display 128. As each new 2D US image is acquired by the TRUS transducer 104 during its rotation, the 3D reconstruction module 148 and 3D display module 144 dynamically update the 3D image presented on the display 128.

The biopsy procedure progresses as follows. After the patient is prepared for the biopsy procedure, a 3D TRUS image is obtained and surveyed by the physician and any observed nodules (suspicious regions) are identified and whether the procedure is a repeat biopsy is noted.

The approach used by the system 100 for registration of the 3D TRUS image with the functional images makes use of an automatic registration method that is based on image intensity features; that is, the normalized mutual information is the image similarity index (NMI). The 3D functional image, such as PET, SPECT, magnetic resonance spectroscopy ("MRS") or optical, acquired at a separate patient imaging session is color coded by converting the grey-scale to a color scale using well-known techniques. The color-coded functional information is then registered automatically to the 3D TRUS image using the following procedure.

For use of the PET or SPECT image, the user loads the 3D CT image, which was acquired together with the PET image using the PET/CT system. Since the 3D CT and PET images are already registered, the user uses the 3D CT image to register with the 3D TRUS using an intensity-based registration procedure (e.g. NMI). This results in registration of the PET image to the 3D TRUS image. For use of an MRS image, the user loads the 3D MRI image, which was acquired together with the MRS image using the MRI/MRS system. Since the 3D MRI and MRS images are already registered, the user uses the 3D MRI image to register with the 3D TRUS image using an intensity-based registration procedure (e.g., NMI). This results in registration of the MRS image with the 3D TRUS image.

All the images are viewed in separate areas of the display, so that they can be examined separately or together. After examining the images, automated alignment and registration of the 3D images is performed by the 3D image registration module 156 to complete the registration.

Figure 10A:
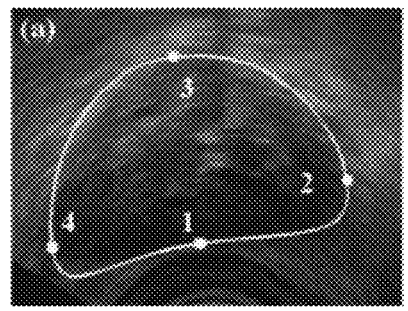
FIGS. 10A and 10B illustrate the segmentation of the prostate in a 2D US image.
Figure 10B:
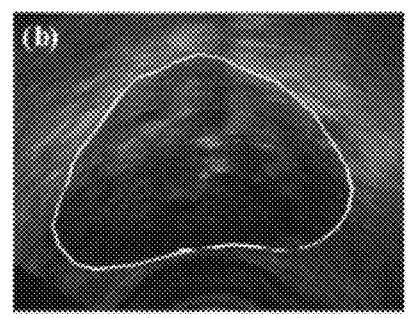

During biopsy planning at step 240, the prostate is segmented in the images. The segmentation of the prostate is described with reference to FIGS. 10A and 10B. The system uses model-based initialization and the discrete dynamic contour to match the initial boundary to the actual prostate boundary, as described in U.S. Pat. No. 6,252,072. An initial prostate boundary is generated by fitting a pre-defined model to four fiducial marks selected by the user along the prostate's edge, as shown in FIG. 10A. The model is then deformed automatically to fit the prostate, as shown in FIG. 10B.

Figure 11:
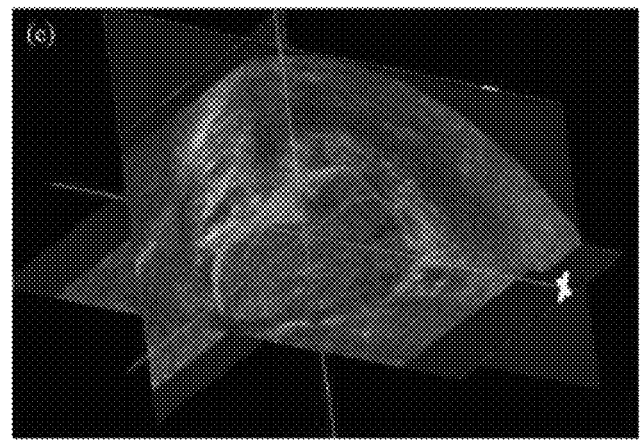
FIG. 11 illustrates a 3D image of a prostate reconstructed from a set of 2D US images.

The 3D TRUS image is sliced into contiguous 2D images, in a parallel or rotational manner. The prostate boundary is segmented in a single 2D image and the result propagated to an adjacent slice repeatedly until the complete 3D prostate is segmented, as shown in FIG. 11.

In addition to the use of the registered 3D functional and TRUS images for planning and targeting the biopsy, additional samples may be required to sample prostate tissue without apparent visible abnormalities, as cancer may be present, but at an early stage not yet visible in the functional or TRUS images.

As discussed above, optimal sampling of the prostate requires knowledge of the prostate size, as using the same number of cores regardless of individual prostate characteristics may lead to over-sampling of small glands, and under-sampling of large glands. In addition, in cases of repeat biopsy, knowledge of the locations of the previous cores helps to plan and guide the repeat biopsy, and help correlate any imaging evidence of the disease. Thus, three important components are required: (1) a method to provide efficient 3D visualization of the prostate, locations of previous cores, and probability distribution of prostate carcinoma; (2) a method to allow planning of the location of the biopsies; and (3) a method to help guide the needles to their targeted locations.

The objective is to provide the radiologist with a: (a) 3D display of the prostate with previous core locations, probability distribution of prostate carcinoma, biopsy target locations, and biopsy planning tools; and (b) a continuously updated needle trajectory in 3D to allow biopsy needle guidance to the targeted locations.

These objectives are met in the guidance and planning phase of the procedure with: (a) a 3D display of all relevant information with superimposed planned needle trajectory before needle insertion; and (b) real-time needle trajectory tracking as the needle is being inserted.

The locations of prior core locations is superimposed on the 3D TRUS image together with the probability distribution of PCa after the current and prior 3D TRUS images have been segmented and registered. To superimpose planned needle trajectories, the known transducer position is used, which is obtained in the same manner as for 3D TRUS imaging. For the free-hand trans-rectal approach, the calibrated geometry of the transducer and its biopsy needle attachment are used to determine the needle trajectory. In the transperineal approach, the needle trajectory is calculated based on the 3D location of the target.

The display provides three orthogonal planes intersecting on the planned needle trajectory. One plane is orthogonal to the needle in an approximate transverse orientation, a second is parallel to the needle in an approximate coronal plane and the third is in a longitudinal plane. As the transducer is moved, the display is updated in real-time showing the appropriate new planned trajectory and prostate planes with the prior core locations and carcinoma probability superimposed.

Nodules, or suspicious regions, are identified using all the images and, using the clinical and biochemical information, are assigned a probability weighting. The probability weighting and recommended biopsy pattern is then color-coded and superimposed on the 3D TRUS image. This image is referred to as a 3D multi-modality probability (3D MMP) image. The 3D MMP image is then used by the physician to select, plan and guide the biopsy procedure.

Figure 9:
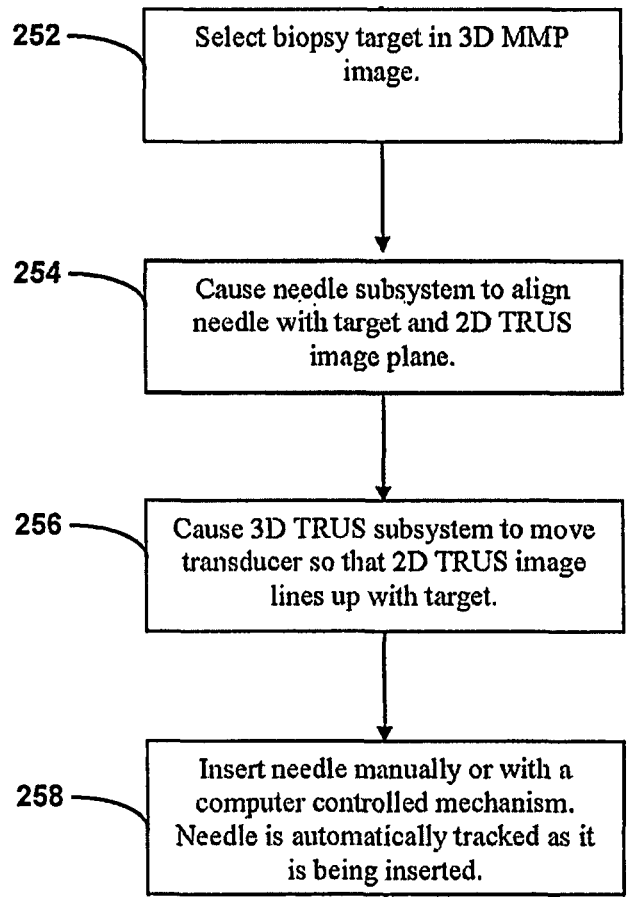
FIG. 9 is a flowchart of the steps performed during needle insertion and guidance in the method of FIG. 6.

FIG. 9 illustrates the steps performed during needle insertion, guidance and tissue sampling during step 250. It is noted that, as steps 230 and 240 are performed in real-time, the 3D TRUS transducer 104 remains positioned inside the patient from the time of capture of the survey image at step 220. A biopsy target is selected in the 3D MMP image (step 252). The system identifies the appropriate template hole and displays the needle path in the 3D MMP image (step 254). The motor assembly 108 causes the 3D TRUS to move so that a 2D TRUS image lines up with the target tissue and needle path (step 256). The optimal 2D US imaging plane for directing the needle 116 into the prostate is chosen by interactively manipulating the US transducer and using the 3D MMP image. This is done by scanning the prostate in real-time with a standard 2D curved array transducer, which has an attached magnetic tracking device. The 2D US image is updated in real-time and displayed in the 3D MMP image for viewing. The operator manipulates the TRUS transducer 104 until the real-time 2D US image intersects the biopsy target. The needle 116 is inserted manually or via a computer-controlled mechanism, and is automatically tracked as it is being inserted (step 258). The lesion is then biopsied using the needle 116.

The image of the needle in the lesion is recorded immediately after the tissue is sampled (e.g., after the needle is fired) and the needle is segmented. The location of the needle tip and the location of the tissue sampling is automatically found, recorded and displayed in the 3D MMP image.

The needle segmentation module 164 is used to segment the needle and its tip in real-time or near real-time and display the result. Using the segmented location of the needle tip, the approximate transverse plane that passes through the needle is displayed. The other two planes are as described above. Thus, with this approach, the radiologist has the usual real-time US image available on the US system monitor, as well as 3D guidance information updated in real-time.

The needle segmentation module 164 and the needle tracking module 172 are used for identifying the needle trajectory and its tip position in 2D and 3D TRUS images. To segment the needle, capture of two 2D or 3D US images are captured. The first (pre-scan) 2D or 3D image is obtained by scanning the prostate (tissue) before the needle is inserted, and the second (post-scan) is acquired by scanning only the region containing the needle during needle insertion. The second 2D or 3D image is compared against the first and the needle position within the post-scan image, including entry point and needle tip location, is determined using a grey-level change detection technique. This approach can segment the needle accurately in real-time for 2D TRUS imaging and in near real-time (i.e., about 5 segmentations per second) for 3D TRUS imaging.

If the targeted lesion was not sampled the procedure is repeated. This process is repeated until all suspicious regions and any other regions of the prostate as identified in the 3D MMP image are biopsied and the biopsy locations are recorded.

While the method of performing biopsy has been described with specificity to manual biopsy needle insertion using a template, other types of biopsy needle insertion methods will occur to those of skill in the art. For example, insertion and/or alignment of the biopsy needle can be performed in a number of manners. In one embodiment, a robotic assembly is used to control the alignment and insertion of the biopsy needle. In another embodiment, a computer is used to control the needle guide in order to control the alignment of the biopsy needle, but still permits manual control of its insertion. In still another embodiment, via a robot or can be computer-controlled.

In a further embodiment, an end-firing US transducer can be coupled to a magnetic tracking device that provides position information to the computer. In this manner, 2D images with position and orientation measurements are simultaneously acquired using a free-hand magnetically tracked approach and are then reconstructed into 3D TRUS images in real-time. A free-hand magnetically or optically tracked scanning approach is used to allow the user to manipulate the transducer freely, and record the position and orientation of the transducer in space. The magnetic tracking approach is based on a small 6 degree-of-freedom magnetic field sensor (receiver) mounted on the TRUS transducer, and a transmitter is placed near the patient to produces a spatially varying magnetic field. The small sensor measures the three components of the local magnetic field strength, and these are used to calculate the TRUS transducer's position and orientation, which are then used in the 3D reconstruction algorithm.

In still yet another embodiment, markers can be attached to the TRUS transducer and a camera tracks movement of the markers in order to determine the position and orientation of the TRUS transducer.

The supplementary volume data can include data from only one source or can include data from a number of sources.

The above-described embodiments are intended to be examples of the present invention and alterations and modifications may be effected thereto, by those of skill in the art, without departing from the scope of the invention which is defined solely by the claims appended hereto.

What is claimed is:

1. A system for performing a prostate biopsy comprising:
   a three-dimensional (3D) trans-rectal ultrasound transducer configured to generate 3D ultrasound image data of a target volume including said prostate;
   a prostate segmentation module for identifying a segmented boundary of said prostate in said 3D ultrasound image data;
   a three-dimensional registration module configured to register said 3D ultrasound image data with a prior acquired 3D image data of said prostate, wherein said prior acquired 3D image data includes previous core locations of biopsy cores registered to the prior acquired 3D image data, wherein said registration is based on at least one of
      image intensity features of corresponding anatomical structures in said 3D ultrasound image data and said prior acquired 3D image data; and
      segmented boundaries of said prostate in said 3D ultrasound image data and said prior acquired 3D image data;
   a display for displaying said 3D ultrasound image data and said previous core locations of said prior acquired 3D image superimposed in the frame of reference of said prostate of said 3D ultrasound image data;
   a biopsy planning module configured to process said 3D ultrasound image data and said previous core locations of said prior acquired 3D image data in combination in order to compute a biopsy plan for said prostate, said biopsy plan including one or more biopsy needle trajectories; and
   a biopsy needle configured to biopsy said prostate in accordance with said computed biopsy plan and following said one or more biopsy needle trajectories.

2. The system of claim 1, further comprising:
   a cancer probability distribution module configured to generate a cancer probability distribution for said prostate.

3. The system of claim 2, wherein said cancer probability distribution module generates said cancer probability distribution based on one or more parameters of a patient.

4. The system of claim 1, wherein said prior acquired 3D image data comprises ultrasound image data captured prior to said biopsy.

5. The system of claim 1, wherein said prior acquired 3D image data comprises a three-dimensional image captured using a modality different than ultrasound imaging.

6. The system of claim 5, wherein said three-dimensional image is captured using single photon emission computerized tomography.

7. The system of claim 5, wherein said three-dimensional image is captured using magnetic resonance spectroscopy.

8. The system of claim 5, wherein said three-dimensional image is captured using positron emission tomography.

9. The system of claim 1, wherein said 3D trans-rectal ultrasound transducer comprises an end-firing trans-rectal ultrasound probe and a computer including a three-dimensional reconstruction module, said three-dimensional registration module and said biopsy planning module, said three-dimensional reconstruction module configured to receive two-dimensional ultrasound image data of the target volume including the prostrate generated by the ultrasound probe and generate the 3D ultrasound image data therefrom.

10. A method for performing a prostate biopsy, comprising:
- acquiring ultrasound image data of a target volume including said prostate using a three-dimensional ultrasound transducer;
- registering said ultrasound image data with prior acquired image data that includes previous core locations of previous biopsy cores registered to the prior acquired image data, wherein said registering is based on at least one of:
  - image intensity features of corresponding anatomical structures in said ultrasound image data and said prior acquired image data; and
  - segmented boundaries of said prostate in said ultrasound image data and said prior acquired image data;
- processing said ultrasound image data and said prior acquired 3D image data in combination in order to compute a biopsy plan for said prostate, said biopsy plan including one or more biopsy needle trajectories; and
- performing a biopsy using a biopsy needle in accordance with said computed biopsy plan and following said one or more biopsy needle trajectories.

11. The method according to claim 10, further comprising:
presenting an image on a display based on said ultrasound image data and said previous biopsy cores of said prior acquired image data.

12. The method of claim 11, wherein said presenting comprises presenting a multi-modality image.

13. The method claim 10, further comprising:
receiving said prior acquired image data from another system.

14. The method of claim 10, further comprising:
capturing said prior acquired image data using a modality different than ultrasound imaging.

* * * * *